(12) United States Patent
Shigekawa et al.

(10) Patent No.: US 7,002,149 B2
(45) Date of Patent: Feb. 21, 2006

(54) DELAY TIME MODULATION FEMTOSECOND TIME-RESOLVED SCANNING PROBE MICROSCOPE APPARATUS

(75) Inventors: Hidemi Shigekawa, Ibaraki (JP); Osamu Takeuchi, Ibaraki (JP); Mikio Yamashita, Hokkaido (JP); Ryuji Morita, Hokkaido (JP)

(73) Assignee: Japan Science and Technology Agency, Saitama (JP)

( * ) Notice: Subject to any disclaimer, the term of this patent is extended or adjusted under 35 U.S.C. 154(b) by 36 days.

(21) Appl. No.: 10/496,571

(22) PCT Filed: Nov. 25, 2002

(86) PCT No.: PCT/JP02/12273

§ 371 (c)(1),
(2), (4) Date: May 24, 2004

(87) PCT Pub. No.: WO03/046519

PCT Pub. Date: Jun. 5, 2003

(65) Prior Publication Data

US 2005/0035288 A1    Feb. 17, 2005

(30) Foreign Application Priority Data

Nov. 26, 2001 (JP) .............................. 2001-360047

(51) Int. Cl.
*H01J 37/00* (2006.01)

(52) U.S. Cl. .................... 250/307; 250/306; 250/423 F

(58) Field of Classification Search ................ 250/306, 250/307, 423 F; 359/326; 356/450
See application file for complete search history.

(56) References Cited

U.S. PATENT DOCUMENTS 4,918,309 A    4/1990 Beha et al.
4,980,566 A  * 12/1990 Heilweil ................ 250/339.07

(Continued)

FOREIGN PATENT DOCUMENTS

| JP | 3145329 | 1/2001 |
|---|---|---|
| JP | 2001-174764 | 6/2001 |
| JP | 3200263 | 6/2001 |

OTHER PUBLICATIONS

V. Gerstner et al.; Journal of Applied Physics, vol. 88, No. 8, pp. 4851-4859. Oct. 15, 2000. Cited in the PCT search report.

(Continued)

*Primary Examiner*—Nikita Wells
*Assistant Examiner*—Johnnie L Smith, II
(74) *Attorney, Agent, or Firm*—Westerman, Hattori, Daniels & Adrian, LLP

(57) ABSTRACT

Disclosed is a measuring apparatus for a physical phenomenon by photoexcitation, in particular a delay time modulated and time-resolved, scanning probe microscope apparatus providing an ultimate resolution both temporal and spatial. The apparatus comprises an ultrashort laser pulse generator (2); a delay time modulating circuit (6) which splits an ultrashort laser pulse (3) produced by the ultrashort laser pulse generator (2) into two and which also modulates a delay time $t_d$ between the two ultrashort laser pulses (4 and 5) with a frequency ($\omega$); a scanning probe microscope (7); and a lock-in detection unit (8) which performs lock-in detection with the delay time modulation frequency ($\omega$) of a probe signal (11) from the scanning probe microscope (7). It can detect the delay time dependency of the probe signal (11) as its differential coefficient to the delay time, with no substantial influence from fluctuations in the intensity of ultrashort laser pulses (3) while preventing the probe apex (19) from thermal expansion and shrinkage by repeated irradiation with ultrashort laser pulses (3). A photoexcited physical phenomenon dependent on a delay time between ultrashort laser pulses can thus be measured at a temporal resolution in the order of femtoseconds and at a spatial resolution in the order of angstroms.

9 Claims, 10 Drawing Sheets

U.S. PATENT DOCUMENTS 5,289,455 A * 2/1994 Kuroda et al. .............. 369/126
5,375,114 A * 12/1994 Hatanaka et al. ........... 369/126
5,416,327 A * 5/1995 Weiss et al. ................ 250/307

OTHER PUBLICATIONS

Hidemi Shigekawa; Journal of the Surface Science Society of Japan, vol. 20, No. 5, pp. 336-343. May 10, 1999. Cited in the PCT search report.

G. Gerber et al.; Springer Series in Chemical Physics, vol. 60, No. 8, pp. 149-151. 1994. Cited in the PCT search report.

U. Keller; Ultrashort Time Optics: An Overview, NATO ASI Series E., vol. 300, pp. 295-305. 1995. Cited in the PCT search report.

W. Pfeiffer et al.; Applied Physics B., vol. 64, No. 2, pp. 265-268. 1997. Cited in the PCT search report.

Koji Sakaguchi; Heisei 10 Nendo Seika Hokokusho, pp. 197-198. 1999. Cited in the PCT search report.

M. Völcker et al.; Physical Review Letters, vol. 66, No. 13, pp. 1717-1720. Apr. 1, 1991. Cited in the PCT search report.

Osamu Takeuchi et al.; Japan J. Appl. Phys. vol. 41, Part I, No. 7B, pp. 4994-4997. Jul. 2002. Cited in the PCT search report.

Stefan Grafström; Journal of Applied Physics, vol. 91, No. 4, pp. 1717-1753. Feb. 15, 2002. Cited in the PCT search report.

Notification of Transmittal of Copies of Translation of the International Preliminary Examination Report dated Jul. 29, 2004 and received by our foreign associate on Aug. 2, 2004.

Feldstein M. J. et al. "Femtosecond optical spectroscopy and scanning probe microscopy" Journal of Physical Chemistry ACS USA, vol. 100, No. 12, Mar. 21, 1996, pp. 4739-4748, XP002316523.

Anonymous: "Time-Resolved Tunneling Microscope" IBM Technical Disclosure Bulletin, vol. 31, No. 11, Apr. 1, 1989, pp. 350-352, XP002316524.

* cited by examiner (a)

(b)

(a)

(b)

DELAY TIME MODULATION FEMTOSECOND TIME-RESOLVED SCANNING PROBE MICROSCOPE APPARATUS

TECHNICAL FIELD

The present invention relates to an apparatus for measuring a physical phenomenon by photoexcitation, which has an ultimate resolution both temporal and spatial. More specifically, the invention relates to a delay time modulated and time-resolved, scanning probe microscope apparatus.

BACKGROUND ART

Attempts to develop next-generation devices having unprecedented functions by controlling structures on nanoscale have been growing rapidly in late years. Among others, creating a functional device and an ultrafast device utilizing photophysical properties is one of particularly important targets. To this end, it becomes necessary and essential to elucidate a photoexcited physical phenomenon in a local area of nanoscale, including a transient response therein. In this connection, it has been proposed to introduce a new measurement technique that combines a scanning probe microscopic technique providing an ultimate spatial resolution with a laser pulse technique providing an ultimate temporal resolution, which has already led to important achievements such as elucidations of photoexcited emission and tunneling current light emission from a single molecule and a semiconductor superlattice structure, an elucidation of a local band structure and an analysis of the point defect. See Journal of Applied Physics Vol.83, No. 7, 1 Apr. 1998, page 3453 ff.; Journal of Applied Physics Vol. 88, No. 8, 15 Oct. 2000, pages 4851; Solid State Communications Vol.6 of 107, page 281 ff., 1998; and Hyomen-Kagaku (Surface Science) 20, page 337 SHIGEKAWA, hidemi "Photoexciting STM".

A scanning probe microscope, e.g., a scanning tunneling microscope, is an apparatus in which the probe apex having a radius of curvature in the order of angstroms is brought proximate to a surface of a specimen across a distance in the order of angstroms and a tunnel junction is formed between the probe apex and the specimen surface to measure a morphology of the surface on an atomic level from a tunneling current passing through the tunnel junction. The scanning tunneling microscope, using a piezo stage that allows scanning with a precision in the order of angstroms, is capable of obtaining a surface morphology at an ultimate spatial resolution.

On the other hand, an ultrashort laser pulse apparatus is an apparatus that is capable of producing a laser pulse having a full width of half maximum in the order of femtoseconds at an ultimate temporal resolution as short as femtoseconds.

If a specimen surface below the probe apex in the scanning tunneling microscope is irradiated with an ultrashort laser pulse to detect a tunneling current synchronized with the ultrashort laser pulse irradiation, it is then possible to measure a photoexcited physical phenomenon at an ultimate resolution both spatial and temporal, thus making it possible to derive the knowledge that is extremely important in creating a nanoscale device.

One such apparatus is a delay time modulated and time-resolved scanning probe microscope apparatus. In this apparatus, a specimen disposed in a scanning probe microscope is irradiated with a series of ultrashort laser pulse pairs for exciting the specimen while the delay time between the two laser pulses in each pulse pair is varied, and the probe signal is measured as a function of the delay time. This apparatus with the ability to measure a transient response of a nanoscale local area to a photoexcited physical phenomenon allows deriving from it the knowledge of the photoexcited physical phenomenon that is needed in creating a functional device and an ultrafast device utilizing photophysical properties. For example, the use of an ultrashort laser pulse capable of exciting a carrier in a small or nanoscale area in a specimen allows determining a lifetime of the carrier from a delay time dependency of a probe signal component that is dependent on the delay time.

Mention is now made of the construction and operation of a conventional time resolved scanning probe microscope apparatus. FIG. 9 shows such a construction of a conventional time-resolved scanning probe microscope apparatus. Here, the scanning probe microscope is illustrated as being a scanning tunneling microscope.

Referring to FIG. 9, ultrashort laser pulses 62 at a given repetition rate from a ultrashort laser pulse generator 60 are split by an interferometric delay circuit 61 into two pulses 63 and 64 having a delay time $t_d$ of 1 ps (picosecond) or so. The pulses 63 and 64 are chopped by a chopper 65 with a frequency ω to be incident on an area on a specimen which lies below a probe 66 in a tunneling microscope unit. A lock-in detection device 69 is used to lock-in-detect a tunneling current signal 67 using a frequency ω (68) as a reference signal to find a difference signal $I_{diff}$ between a tunneling current $I_{irr}$ at the time of irradiation and a tunneling current $I_{bak}$ at the time of non-irradiation. This measurement is repeated while continuously changing the delay time $t_d$ between the ultrashort laser pulses 63 and 64 to determine the delay time dependency of the tunneling current component $I_{diff}$ that is dependent on the delay time.

The conventional apparatus mentioned above has presented problems as described below, however.

First, the probe signal component that is dependent on the delay time $t_d$ is much smaller than the component that is not dependent on the delay time $t_d$, and cannot be measured with enough precision even if the dynamic range of the lock-in device is increased to its limit.

Second, the light output intensity of the ultrashort laser light pulse generator has a long-period fluctuation due to a small change in environment (such as temperature etc.) which fluctuation, however, cannot be eliminated by the conventional technique; hence it is hard to determine the delay time dependency of the probe signal at sufficient precision.

Thus, as far as the conventional technique is concerned in which a difference in probe signal between when light is irradiated and when it is not irradiated is relied on, it has been found to be difficult to measure the delay time dependency of the probe signal component at sufficient sensitivity and precision.

Third, the probe apex in the scanning probe microscope, when irradiated with ultrafast laser pulses, is thermally elongated, while it shrinks when the laser pulses are turned off. This results in changes in the spacing between the probe apex and specimen surface and in turn in changes in the tunneling probability between them. Thus, here again there ensues the difficulty in measuring the delay time dependency of the probe signal at both high sensitivity and high precision.

Also in the prior-art apparatus, ultrashort laser pulses 63 and 64 having a delay time $t_d$ have an identical wavelength as shown in FIG. 9. Thus, while such an apparatus permits measuring a phenomenon in which two energy levels participate, it cannot measure a photoexcited phenomenon in which three or more energy levels take parts.

Assuming, for example, that as shown in FIG. 10 there are excited states through energy levels 71, 72 and 73, there is a case that when a carrier upon absorbing a light energy corresponding to a difference in energy between the level 71 and the level 73 is excited from the level 71 to the level 73, the relaxation time is sought to be known of this carrier relaxing to the level 72 from the level 73. In this case, the relaxation time can be found by irradiating a specimen with a light pulse 74 having an energy corresponding to a difference in energy between the level 71 and the level 73 and a light pulse 75 having an energy corresponding to a difference in energy between the level 72 and the level 73 while continuously varying the delay time $t_d$ between these pulses and determining the delay time dependency of the probe signal component. However, the prior-art apparatus cannot have two short light pulses that have different wavelength to each other.

With the view to solving the abovementioned problems, it is a first object of the present invention to provide a delay time modulated and time-resolved scanning probe microscope apparatus whereby a probe signal component that is dependent on a delay time can be measured directly at both high sensitivity and high precision with a femtosecond resolution, without the need for an increased dynamic range in a lock-in detection unit, without necessitating a probe signal value while an ultrashort laser pulse is not irradiated, with no substantial influence from a long-period fluctuation in light output intensity in an ultrashort laser pulse generator and with no substantial change in tip-specimen distance in a scanning probe microscope.

With the view to solving the abovementioned problems, it is also a second object of the present invention to provide a delay time modulated and time-resolved scanning probe microscope apparatus whereby plural ultrashort laser pulses that excites the specimen can have different wavelengths to each other, whose delay time is controlled can be varied in a manner as desired.

DISCLOSURE OF THE INVENTION

In order to achieve the first object mentioned above, there is provided in accordance with the present invention as set forth in claim 1 a delay time modulated and femtosecond time-resolved scanning probe microscope apparatus, characterized in that it comprises: an ultrashort laser pulse generator; a delay time modulating circuit for splitting an ultrashort light pulse produced by the said ultrashort laser pulse generator into two ultrashort laser pulses interspaced by a delay time while establishing a value for the delay time between the two ultrashort laser pulses and modulating the delay time centering about the established value with a fixed modulation frequency; a scanning probe microscope for scanning a specimen over a surface area thereof with a probe wherein the probe is disposed just above the specimen so that a tunnel junction is formed between a probe apex and a surface of the said specimen when irradiated with the said two ultrashort laser pulses modulated by the said delay time modulating circuit; and a lock-in detection unit for lock-in-detecting a probe signal of the specimen irradiated with the said ultrashort laser pulses in the said scanning probe microscope using the modulation frequency for the delay time.

In the construction mentioned above, the said ultrashort laser pulse generator may be adapted to produce a series of ultrashort laser pulses having a pulse width in the order of femtoseconds at a fixed periodicity. Further, the said delay time modulating circuit preferably includes a half mirror and two sets of movable mirrors of which each set comprises mirrors fastened to a piezo stage wherein at least one of the said sets of movable mirrors is adapted to be driven to change a center value of the delay time and to modulate the delay time as a center delay time with the fixed frequency. The said lock-in detection unit may be adapted to perform lock-in detection using the modulation frequency as a reference frequency.

According to the construction mentioned above, the ultrashort laser pulse generator produces at a fixed periodicity ultrashort laser pulses having a pulse width in the order of femtoseconds, each of which is split by a half mirror in the delay time modulating circuit into two ultrashort laser pulses. These two ultrashort laser pulses are reflected by two sets of movable mirrors fastened to a piezo stage, respectively, and then are again brought together through the half mirror. In this course, the delay time between the two ultrashort laser pulses is set at a desired value by adjusting the difference between the respective lengths of the turn-around optical paths with the two sets of movable mirrors, and the length of the optical path with one of the two sets of movable mirrors is modulated with a selected amplitude and a selected frequency. The two ultrashort laser pulses having the delay time modulated with the selected amplitude and frequency centering around the set delay time value are incident on the specimen just below the probe in the scanning probe microscope to change the energy state of the specimen, resulting in a change in the probe signal.

The lock-in detection unit performs lock-in detection using the delay time modulation frequency as a reference frequency and detects a quantity that is proportional to the differential coefficient of the probe signal on the delay time between the two ultrashort laser pulses. The measurement is repeated by continuously changing the delay time.

From the quantity that is proportional to the differential coefficient of the probe signal to the delay time between the ultrashort laser pulses there can be found by computation the differential coefficient of the probe signal to the delay time between the ultrashort laser pulses. Integrating this differential coefficient with the delay time allows finding the dependency of the probe signal on the delay time.

Since the ultrashort laser pulse generator provides a temporal resolution in the order of femtoseconds and the delay time modulating circuit uses a piezo stage, it is possible to set the delay time at a temporal resolution in the order of femtoseconds. Since the lock-in detection unit which uses the delay time modulation frequency as its reference frequency for lock-in detection detects the quantity that is proportional to the differential coefficient of the probe signal to the delay time between the ultrashort laser pulses, namely detecting the differential coefficient of the probe signal to the delay time between the ultrashort laser pulses directly, it is possible to measure at both high sensitivity and high precision a delay time dependent, minute component of the probe signal even if it contains a large background component.

Further, making the delay time modulation frequency much higher than the frequency of fluctuations in intensity of ultrashort laser pulses allows a delay time dependent, minute component of the probe signal to be detected unaffected by such fluctuations in intensity of ultrashort laser pulses.

Furthermore, irradiating the specimen just below the probe with all the ultrashort laser pulses produced in a train by the ultrashort laser pulse generator at a fixed periodicity—rather than with those in part interrupted such as by a chopper as in the prior art—while making the frequency of ultrashort laser pulses produced much higher than the thermal response frequency at the probe apex permits the probe apex to be supplied with ultrashort light pulses continuously and with no time in which it is allowed to cool and thus to hold its temperature substantially constant. This will prevent the probe apex from repeatedly thermally expanding and contracting, prevent its distance from the surface of the specimen from changing and eventually prevent the tunneling probability from fluctuating. As a result, it is made possible to measure a delay time dependent, minute component of the probe signal at both high sensitivity and high precision. Also, the use of the scanning probe providing a spatial resolution in the order of angstroms allows a delay time dependent, minute component of the probe signal to be detected at a spatial resolution in the order of angstroms, hence at both high sensitivity and high precision.

Thus, according to the present invention that allows a probe signal component dependent on a delay time between exciting light pulses at a spatial resolution in the order of angstroms and at a temporal resolution in the order of femtoseconds to be directly measured at high sensitivity and precision, it becomes possible to measure a photoexcited physical phenomenon at an ultimate resolution both spatial and temporal.

In order to achieve the second object mentioned above, there is also provided in accordance with the present invention as set force in claim 6 a delay time modulated and femtosecond time-resolved scanning probe microscope apparatus, characterized in that it comprises: an ultrashort laser pulse generator; an ultrabroadband, variable wavelength, multi-pulse waveform shaping unit (see PCT International Publication No. WO 01/44863 A1) for producing from an ultrashort laser pulse produced by the said ultrashort laser pulse generator, a plurality of ultrashort light pulses each of that can have different wavelength to others and interspaced by a delay time and establishing a desired value for the delay time between the ultrashort laser pulses different in wavelength; a wavelength/delay time/modulation timing control unit for producing a control signal to establish selected values for the wavelength of the ultrashort laser pulses, a control signal to establish a selected value for the delay time between the ultrashort laser pulses and a control signal to modulate the delay time at selected time instants, and delivering such control signals to a two-dimensional space amplitude modulator and a two-dimensional space phase modulator in the said ultrabroadband, variable wavelength, multi-pulse waveform shaping unit while furnishing a lock-in detector with delay time modulation timing signals used as a reference signal for lock-in detection thereby; a scanning probe microscope for scanning a specimen over a surface area thereof with a probe wherein the probe is disposed just above the specimen so that a tunnel junction is formed between a probe apex and a surface of the said specimen when irradiated with the said ultrashort laser pulses controlled by the said wavelength/delay time/modulation timing control unit and transmitted from the said ultrabroadband, variable wavelength, multi-pulse waveform shaping unit; and a lock-in detection unit for lock-in-detecting a probe signal of the specimen irradiated with the said ultrashort laser pulses in the said scanning probe microscope using the said modulation timing signals as the reference signal.

The said wavelength/delay time/modulation timing control unit may be characterized in that it comprises a computer that is responsive to input values for desired wavelengths of and delay time between the said ultrashort laser pulses and an input value for a modulation timing frequency for computing control signals for the said two-dimensional space amplitude and phase modulators and transmitting these control signals thereto while furnishing the said lock-in detection unit with the said modulation timing signals.

The said lock-in detection unit may be characterized in that it is configured to perform lock-in detection using the said modulation timing as a reference frequency and thereby to detect a quantity that is proportional to a differential coefficient of the said probe signal with respect to said delay time. The said scanning probe microscope may be characterized in that it is a scanning tunneling microscope or an atomic force microscope.

With the apparatus constructed as mentioned above, a probe signal component that is dependent on a delay time between exciting light pulses at a spatial resolution in the order of angstroms and at a temporal resolution in the order of femtoseconds can be directly measured at both high sensitivity and high precision as with the delay time modulated and femtosecond time-resolved scanning microscope apparatus as set forth in claim 1. Moreover, it permits a probe signal component that is dependent on a delay time between exciting light pulses different in wavelength and of wavelengths as desired to be directly measured at high sensitivity and precision. Accordingly, it makes it possible for a photoexcited physical phenomenon in which three or more energy levels take parts to be measured at an ultimate resolution both spatial and temporal.

BRIEF DESCRIPTION OF THE DRAWINGS

The present invention will better be understood from the following detailed description and the drawings attached hereto showing certain illustrative forms of implementation of the present invention. In this connection, it should be noted that such forms of implementation illustrated in the accompanying drawings hereof are intended in no way to limit the present invention but to facilitate an explanation and understanding thereof. In the drawings, in connection with the first object.

Figure 5:
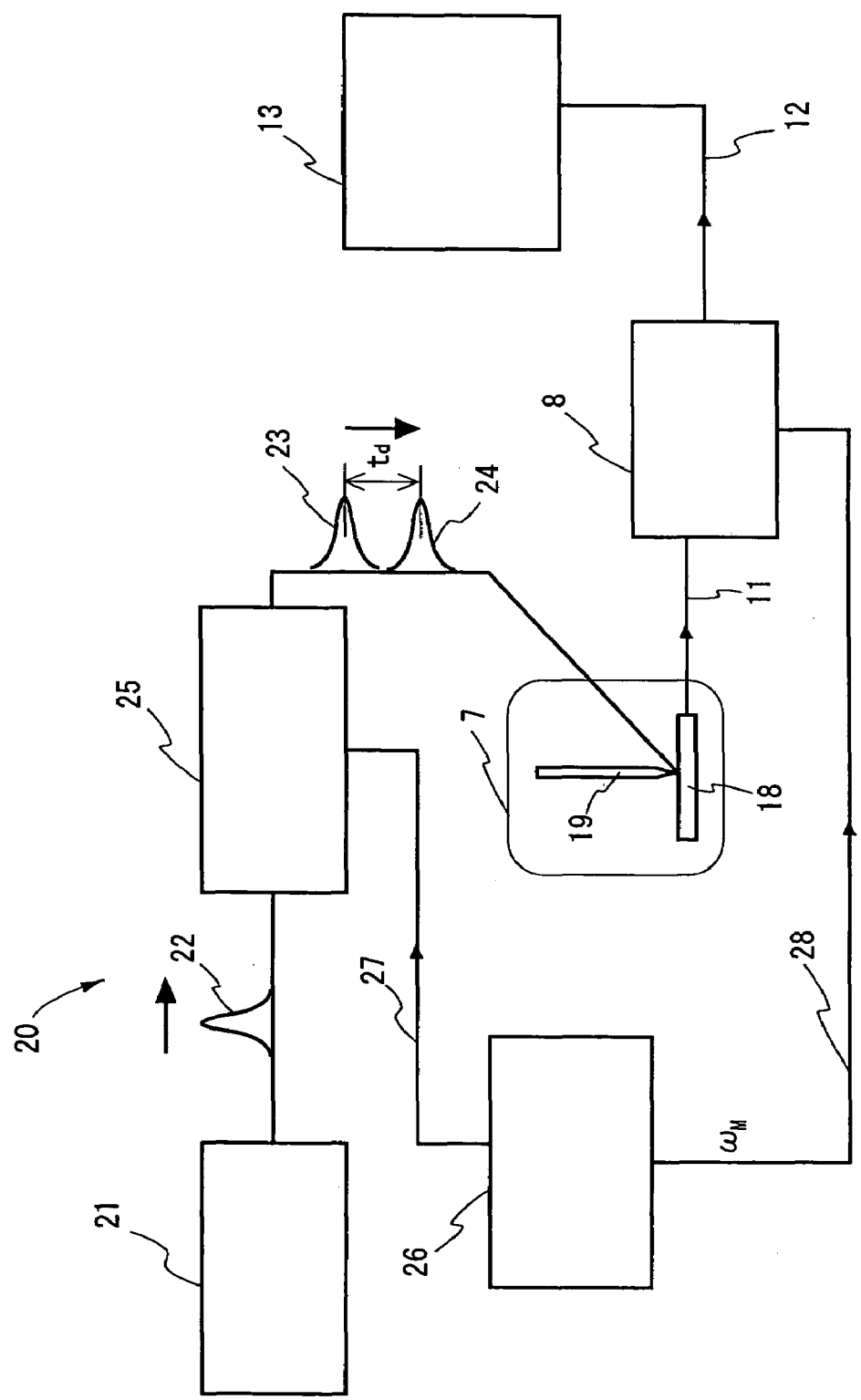
Figure 6:
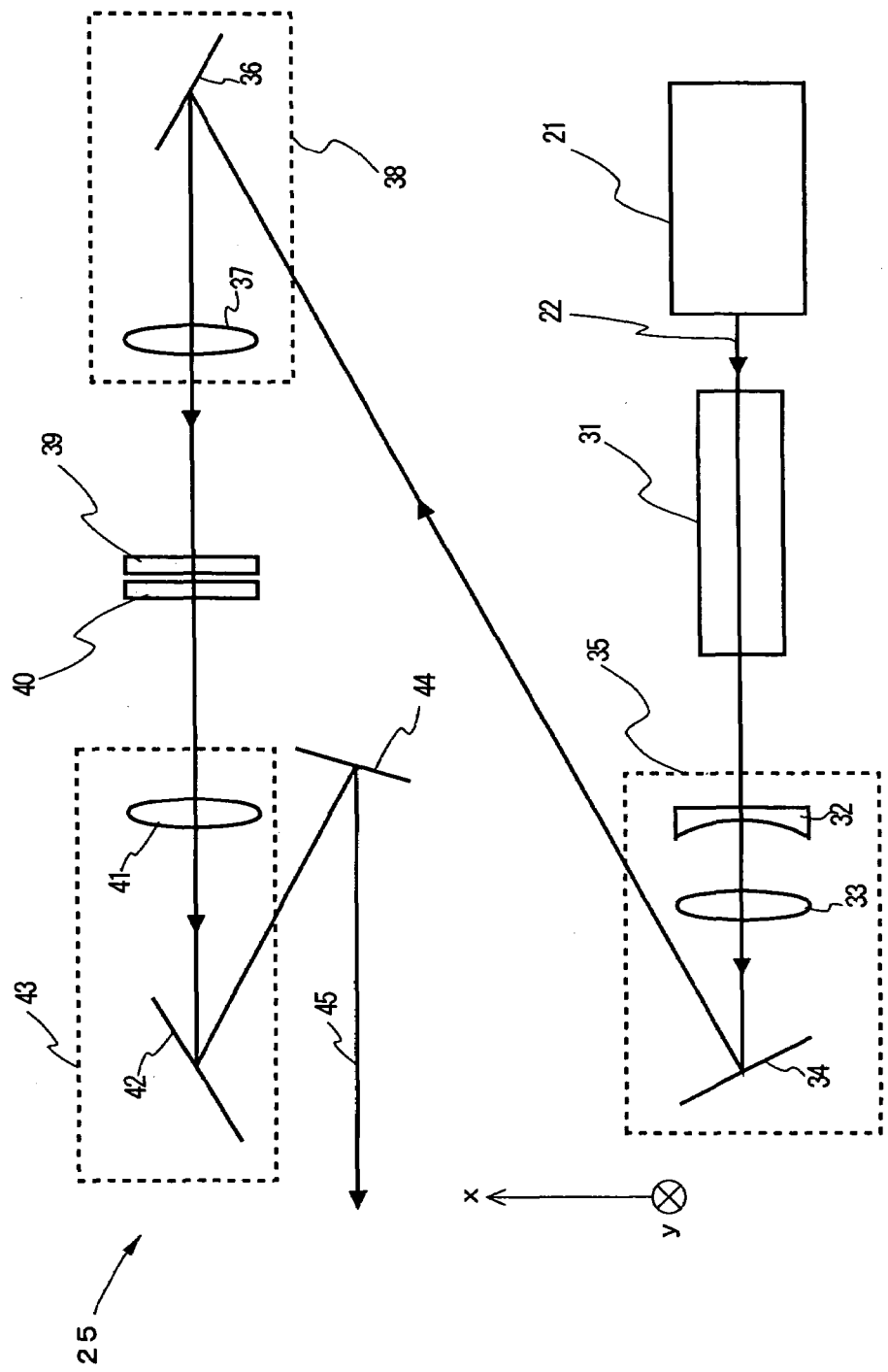
Figure 7:
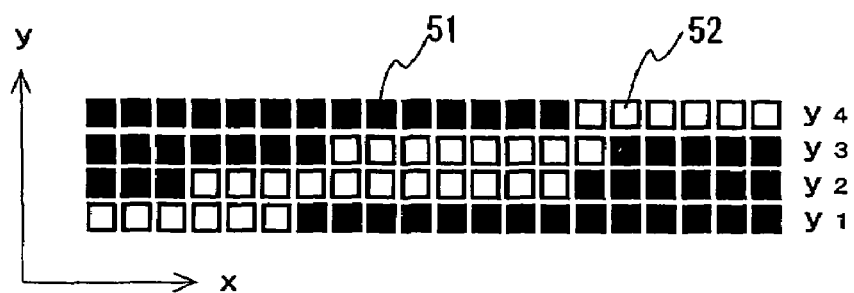
Figure 7:
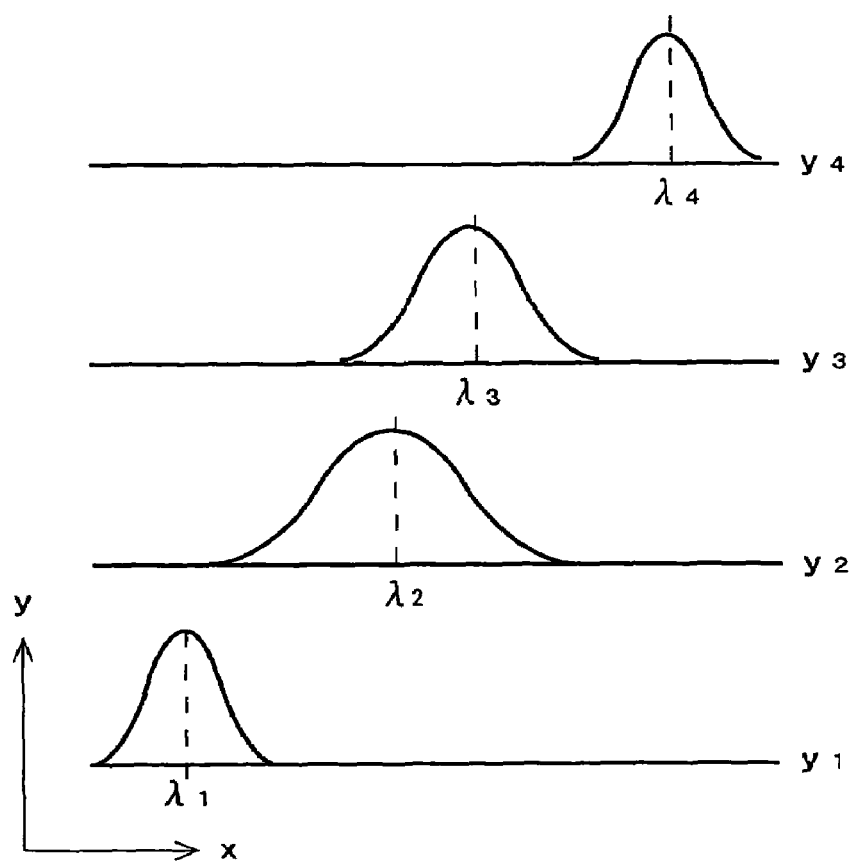
Figure 8:
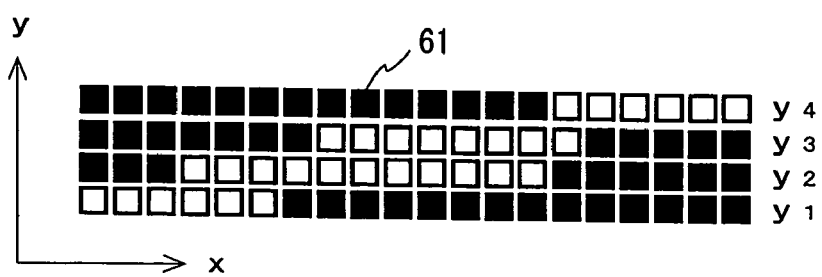
Figure 8:
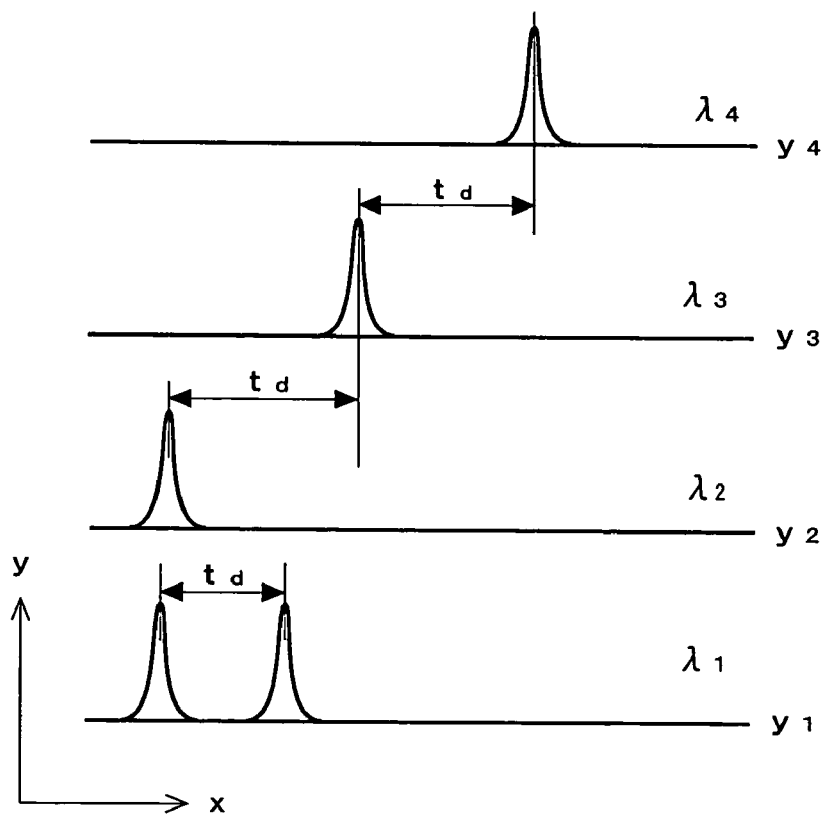
Figure 9:
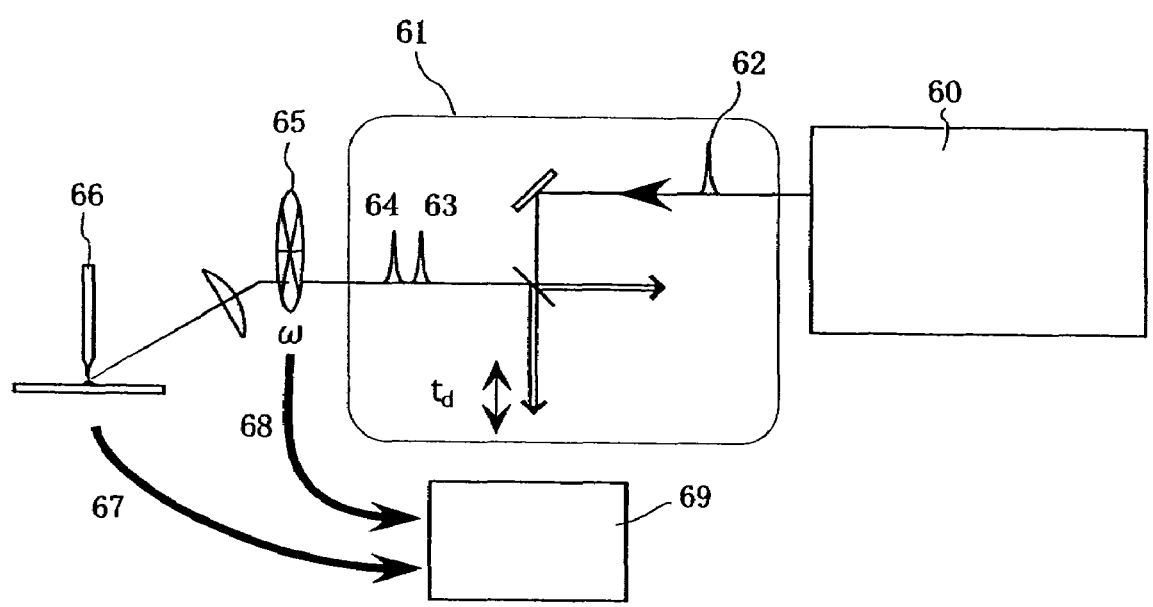

And in connection with the second object:

FIG. 5 is a diagram illustrating the construction of a delay time modulated and femtosecond time-resolved scanning probe microscope apparatus constituting a second form of implementation of the present invention;

FIG. 6 is a diagram illustrating the makeup of an ultrabroadband, variable wavelength, multi-pulse waveform shaping unit;

FIG. 7 is a diagram illustrating an example of how the transmissivity of a two-dimensional space amplitude modulator may be set;

FIG. 8 is a diagram illustrating an example of how the phase of a two-dimensional space phase modulator may be set;

FIG. 9 is a diagram illustrating the makeup of the prior-art apparatus; and

Figure 10:
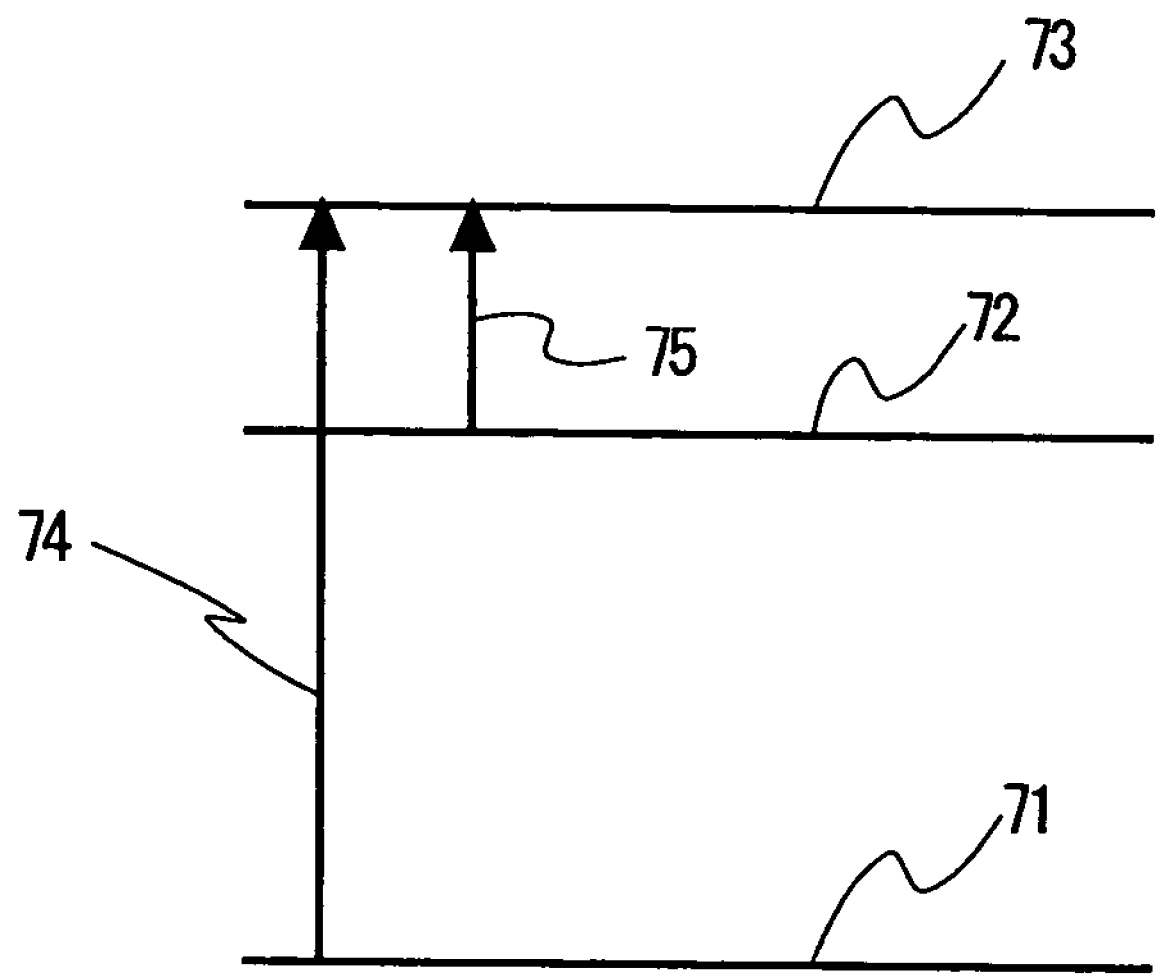

FIG. 10 is a diagram illustrating excitation in a three-level system.

BEST MODES FOR CARRYING OUT THE INVENTION

Hereinafter, the present invention will be described in detail with reference to certain suitable forms of implementation thereof illustrated in the drawing figures.

Mention is first made of a delay time modulated and femtosecond time-resolved scanning probe microscope apparatus constituting a first form of implementation of the present invention.

Figure 1:
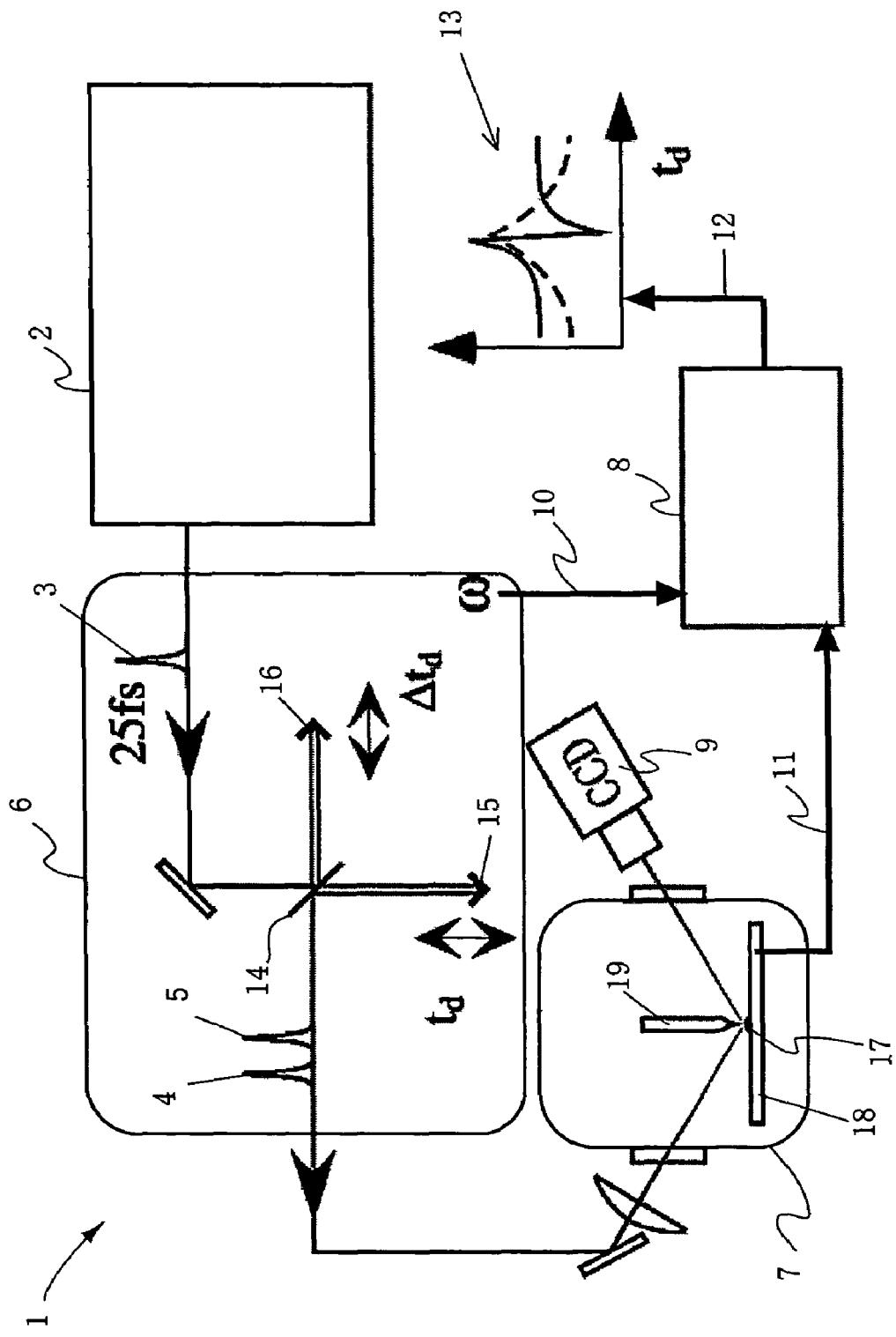
FIG. 1 is a diagram illustrating the construction of a delay time modulated and femtosecond time-resolved scanning probe microscope apparatus constituting a first form of implementation of the present invention.

FIG. 1 is a diagram illustrating the construction of a delay time modulated and femtosecond time-resolved scanning probe microscope apparatus constituting a first form of implementation of the present invention. In the Figure, the delay time modulated and femtosecond time-resolved scanning probe microscope apparatus of the present invention designated by reference numeral 1 comprises an ultrashort laser pulse generator 2 for producing a series of ultrashort laser pulses 3; a delay time modulating circuit 6 which splits an ultrashort laser pulse 3 produced by the ultrashort laser pulse generator 2 into two ultrashort laser pulses 4 and 5 and which also modulates a delay time $t_d$ between ultrashort laser pulses 4 and 5 with a frequency $\omega$; a scanning probe microscope 7 for scanning a specimen 18 over a surface area thereof with a probe 19 in which the probe 19 is disposed just above the specimen 18 so that a tunnel junction is formed between a probe 19's apex and the specimen 18 irradiated with the ultrashort laser pulses 4 and 5 with the delay time $t_d$ modulated with the frequency $\omega$; and a lock-in detection unit 8 which performs lock-in detection with the modulation frequency $\omega$ of a probe signal 11 that is a tunneling current passing between the probe 19's apex and the specimen 18 and modulated by irradiation of the ultrashort laser pulses 4 and 5 thereon.

In the Figure, designated by reference numeral 9 is a CCD camera that aids in the setup of the scanning probe, and reference numerals 10 and 11 indicate the reference frequency ($\omega$) signal transmitted from the delay time modulating circuit 6 into the lock-in detection unit 8, and the probe signal transmitted from the scanning probe microscope 7 into the lock-in detection unit 8, respectively. Measurement data 12 are transmitted from the lock-in detection unit 8 into an image display (not shown) where they are displayed in the form of, e.g., what is indicated by reference numeral 13.

The ultrashort laser pulse generator 2 produces an ultrashort laser pulse 3 having a pulse width in the order of femtoseconds recurrently at a fixed periodicity. It may be, for example, a Ti/sapphire laser that generates an ultrashort laser pulse of a wavelength of 800 nm (nanometer) and a pulse full width of half maximum of 25 fs (femtosecond) and at a repetition frequency of 80 MHz.

The delay time modulating circuit 6 includes a half mirror 14 that splits the ultrashort laser pulse 3 into a first and a second ultrashort laser pulse 4 and 5 which travel respectively in a first and a second direction orthogonal to each other, and two sets of movable mirrors 15 and 16 provided in those directions in which the ultrashort laser pulses 4 and 5 travel, respectively. Each set of movable mirrors 15 and 16 can be driven by a piezo stage to adjust its spacing from the half mirror 14 as desired and also to oscillate with an amplitude as desired and at a frequency ($\omega$) as desired. In the embodiment illustrated, the movable mirror 15 is used to adjust the center delay time $t_d^{(0)}$ and the movable mirror 16 to apply the frequency modulation (with amplitude $\Delta t_d$ and at frequency $\omega$).

The scanning probe microscope 7 may be one in which the probe 19's apex having a radius of curvature in the order of angstroms can be brought proximate to a specimen surface across a spacing in the order of angstroms and which is capable of scanning the specimen surface with a precision in the order of angstroms. It is preferably a scanning tunneling microscope or an atomic force microscope for very low temperature and ultrahigh vacuum using, e.g., a piezo stage. The lock-in detection unit may be a conventional one, preferably having a large dynamic range.

The apparatus mentioned above operates as stated below.

The ultrashort laser pulse generator 2 produces an ultrashort laser pulse 3 having a pulse width in the order of femtoseconds recurrently at a fixed periodicity, and each ultrashort laser pulse 3 is split by the half mirror 14 in the delay time modulating circuit 6 into two ultrashort light pulses 4 and 5 which are separately reflected by the two sets of movable mirrors 15 and 16 and then brought together by the half mirror 14. Then, the center delay time $t_d^{(0)}$ between two ultrashort laser pulses 4 and 5 is set at a selected value by adjusting the difference between the turnaround optical path lengths with the movable mirror sets 15 and 16 while the optical path length with one movable mirror set 16 is modulated with a selected amplitude $\Delta t_d$ and a selected frequency $\omega$. The two ultrashort laser pulses 4 and 5 with the delay time modulated with the selected amplitude $\Delta t_d$ and the selected frequency $\omega$ and centering around the center delay time $t_d^{(0)}$ are incident on a gap 17 just below the probe in the scanning probe microscope 7 and change the energy state of the specimen 18, thereby changing the probe signal 11.

The lock-in detection unit 8 performs lock-in detection using the modulation frequency $\omega$ of the delay time as a reference frequency and detects a quantity that is proportional to a differential coefficient of the probe signal 11 with respect to the delay time ($dI_t/dt_d$). To wit, $I_t$, the probe signal at time t when the delay time between the ultrashort laser pulses 4 and 5 is modulated, centering around the center delay time $t_d^{(0)}$, with the amplitude $\Delta t_d$ and the frequency $\omega$ is expressed by equation (1) as follows:

$$I_t(t_d^{(0)} + \Delta t_d \sin \omega t) = I_t(t_d^{(0)}) + \Delta t_d \sin \omega t \frac{dI_t}{dt_d}\bigg|_{t_d=t_d^{(0)}} + o^2(\Delta t_d \sin \omega t) \quad (1)$$

and the lock-in detection with the reference frequency $\omega$ gives rise to the detection of the coefficient of sin $\omega$ t in the second term of the right side of equation (1), namely $$\Delta t_d \frac{dI_t}{dt_d}\bigg|_{t_d=t_d^{(0)}}. \quad (2)$$

Since the amplitude $\Delta t_d$ is known, from this coefficient there can be found the differential coefficient of the probe signal to the delay time, ($dI_t/dt_d$). It is thus possible to find the dependency of the probe signal $I_t$ on the delay time $t_d^{(0)}$ between the ultrashort laser pulses 4 and 5, by continuously changing the center delay time $t_d^{(0)}$ to measure the differential coefficient ($dI_t/dt_d$) and then integrating the same. This method whereby fluctuating background components have been eliminated allows finding the delay time dependency of the probe signal at both high sensitivity and high precision.

Since the ultrashort laser pulse generator 2 provides a temporal resolution of femtoseconds and the delay time modulating circuit 6 uses a piezo stage as mentioned above, it is here possible to set the delay time at a temporal resolution of femtoseconds. Further, since the lock-in detection unit 8 performs lock-in detection using the modulation frequency ω as its reference frequency to directly detect a quantity that is proportional to a differential coefficient of the probe signal to the delay time with the result that fluctuating background components have been eliminated, the delay time dependency of the probe signal that is dependent on the delay time can be measured at a temporal resolution of femtoseconds, hence at both high sensitivity and high precision.

Further, making the modulation frequency ω of the delay time much higher than the fluctuation frequency of the ultrashort laser pulse intensity allows the delay time dependency of the probe signal to be measured unaffected by the fluctuation frequency of the ultrashort laser pulse intensity.

Furthermore, irradiating the specimen just below the probe with all the ultrashort laser pulses 3 produced in a train by the ultrashort laser pulse generator 2 at a fixed periodicity—rather than with those in part interrupted such as by a chopper as in the prior art—while making the frequency of ultrashort laser pulses 3 produced much higher than the thermal response frequency at the probe 19's apex permits the probe 19's apex to be supplied with ultrashort laser pulses 4 and 5 with no time in which it is allowed to cool and thus to hold its temperature substantially constant. This will prevent the probe 19's apex from repeatedly thermally expanding and contracting, prevent its distance from the surface of the specimen 18 from changing and eventually prevent the tunneling probability from fluctuating. As a result, it is made possible to measure the delay time dependency of the probe signal 11 at both high sensitivity and high precision.

Moreover, the use of a scanning probe microscope 7 providing a spatial resolution in the order of angstroms allows the measurement at a spatial resolution in the order of angstroms.

Next, Specific Example 1 is shown.

This Example is to show that the apparatus of the present invention prevents the probe apex of a scanning probe from thermal expansion and shrinkage.

Figure 2:
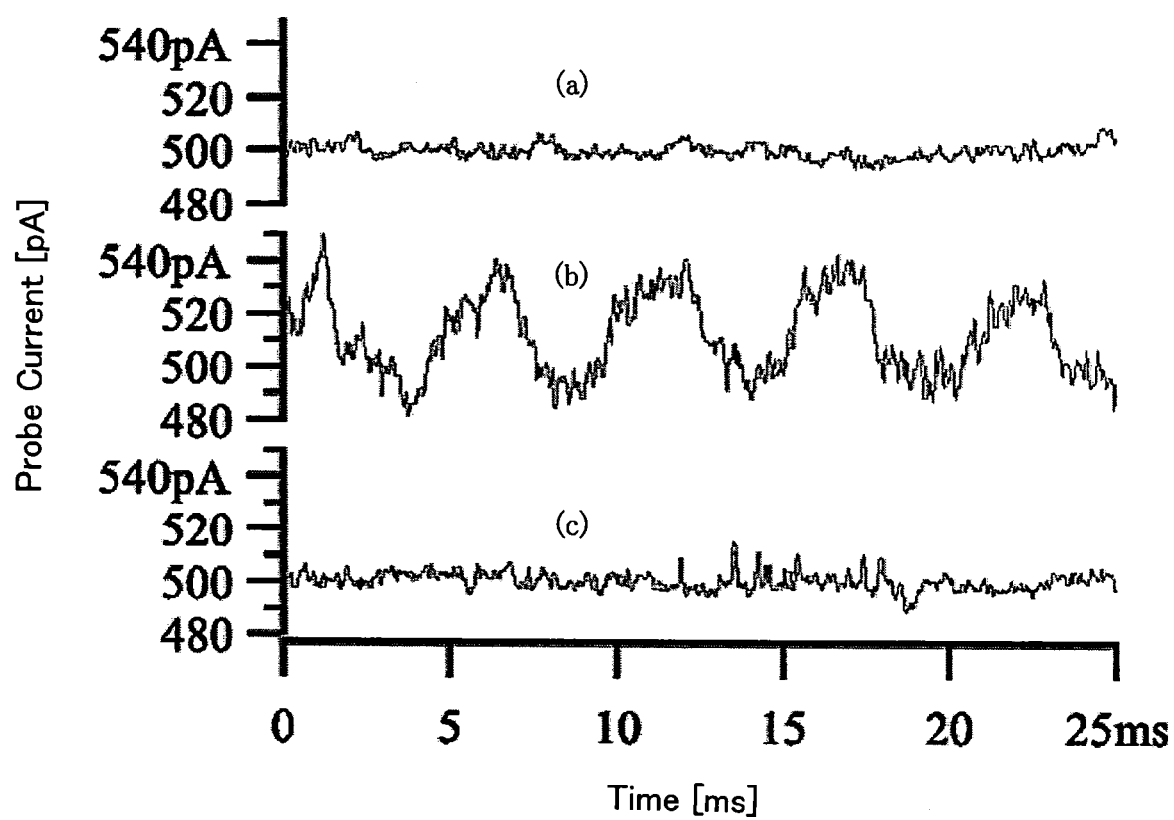
FIG. 2 is a diagram illustrating results of measurement of the probe signal flowing through a Au (111) thin film deposited on mica in an apparatus of the present invention.

FIG. 2 is a diagram illustrating results of measurement of the probe signal flowing through a Au (111) thin film deposited on mica in the present apparatus. The ultrashort laser pulse generator makes use of a Ti: sapphire laser that produces an ultrashort laser pulse having a wavelength of 800 nm and a pulse full width of half maximum of 25 fs recurrently at a repetition frequency of 80 MHz. Au is a material that does not exhibit absorption for a light wavelength of 800 nm and the probe signal is predicted not to fluctuate in a measurement.

FIG. 2(*a*) is a graph showing the probe signal (tunnel current) as a function of time without the light irradiation, from which it is seen that the probe signal then does not change with time. FIG. 2(*b*) is a graph showing the probe signal that is measured when the laser light is chopped at a frequency of 200 Hz to irradiate, from which graph it is seen that the probe signal fluctuates at a cycle of 5 ms (millisecond), indicating that the probe apex of the scanning probe is thermally expanded and contracted by the laser pulse irradiation, thereby fluctuating the probe signal. FIG. 2(*c*) is a graph showing the probe signal that is measured when the delay time is modulated with a delay time modulation amplitude $\Delta t_d$ of 400 fs and a modulation frequency ω of 100 Hz, from which graph it is seen that the probe signal does not change with lapse of time. It is thus seen that the present apparatus does not cause the probe apex of the scanning probe to be thermally expanded and contracted by the laser pulse irradiation.

Next, Specific Example 2 is shown.

Figure 3:
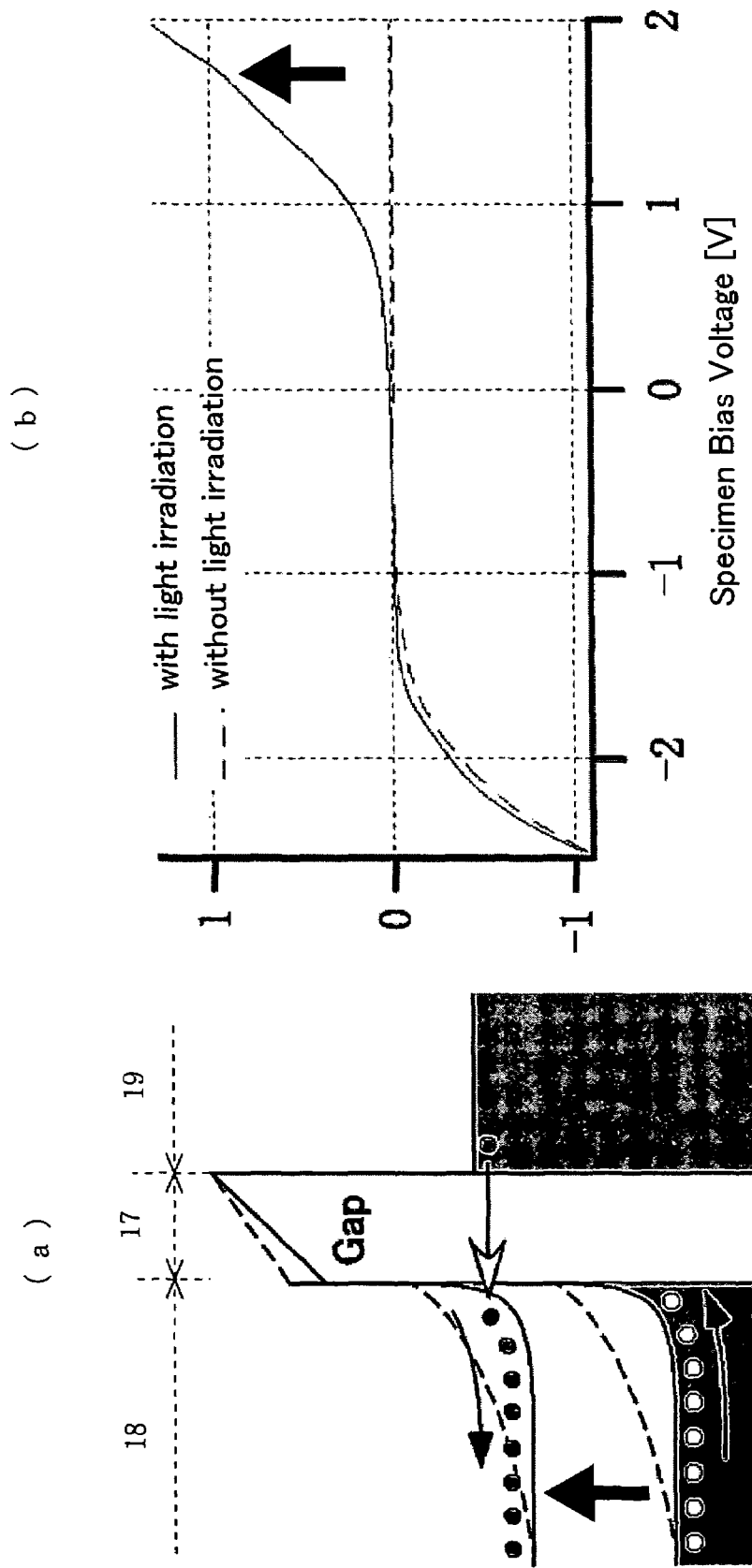
FIG. 3 is a diagram showing a measurement system used to evaluate the temporal resolution of an apparatus according to the present invention.

This Example is to show a temporal resolution of the present apparatus. FIG. 3 is a diagram showing a measurement system used to evaluate the temporal resolution of the present apparatus. The specimen was made of an n-type GaAs (100) substrate. In this connection it should be noted that the lifetime of the carrier of n-type GaAs is sufficiently long so that it may be little relaxed within a range of the delay time in this Example. FIG. 3(*a*) is a diagram showing an energy band structure made of the specimen 18 of n-type GaAs, the probe 19's apex and a gap 17 between the specimen 18 and the probe 19's apex. FIG. 3(*b*) is a diagram showing the change of the probe signal (plotted along the ordinate axis) with respect to the bias voltage (plotted along the abscissa axis) which is applied between the probe 19's apex and the n-type GaAs 18 with the former taken as a basis in the makeup of FIG. 3(*a*). In the diagram, the broken lines indicate the case without the light irradiation while the solid lines indicate the case where it is applied. If the specimen bias voltage is negative, the Schottky barrier that is formed at the tunneling gap is biased in the forward direction, which is followed by a rise in the tunneling probability such that electrons tunnel from the n-type GaAs 18 into the probe 19's apex and probe signal flows from the latter into the former. This state corresponds to what the broken curve in the region of negative voltage in FIG. 3(*b*) indicates. If the voltage is positive, as shown by the broken lines in FIG. 3(*a*) the existence of the energy barrier near the surface of the n-type GaAs 18 holds the tunneling probability small so that no probe signal flows into the n-type GaAs 18 from the probe 19's apex. This state corresponds to what is indicated by the broken line in the region of positive voltage in FIG. 3(*b*). If the light irradiation is applied when the voltage is positive, carriers are then excited as indicated by the black solid arrow in FIG. 3(*a*) to make thinner the energy barrier near the surface of the n-type GaAs 18, which is followed by a rise in the tunneling probability such that electrons tunnel from the n-type GaAs 18 into the probe apex 19 and probe signal flows from the latter into the former. This state corresponds to what the solid curve indicates (as the black solid arrow points) in the region of positive voltage in FIG. 3(*b*).

Figure 4:
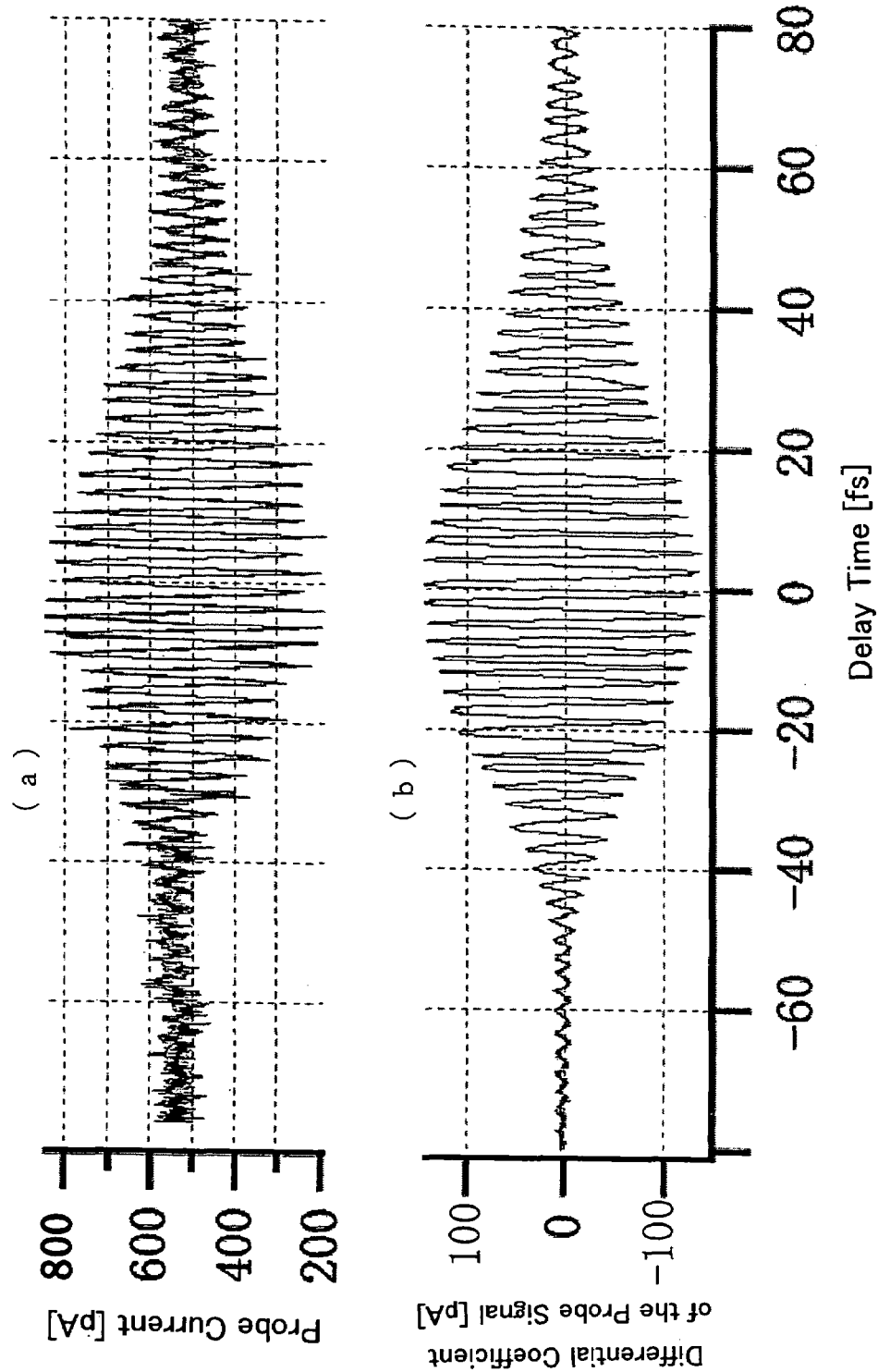
FIG. 4 is a graph showing the temporal resolution of an apparatus according to the present invention.

In this Example, the temporal resolution of the present apparatus was evaluated using a system in which the above-mentioned voltage is positive. FIG. 4 is a graph showing a temporal resolution of the present apparatus. FIG. 4(*a*) indicates the probe signal (plotted along the ordinate axis) with respect to the delay time $t_d^{(0)}$ (plotted along the abscissa axis) between the ultrashort laser pulses split into two. Measurements were taken while increasing (and decreasing) the delay time $t_d^{(0)}$ incrementally by about 1 fs from $t_d^{(0)}=0$, namely where the two ultrashort laser pulses overlap. As is apparent in the graph, it is seen from the fact that the probe signal oscillates with a cycle of 2.68 fs corresponding to a wavelength of 800 nm of the ultrashort laser pulses that the probe signal oscillates responsive to interference intensities of the two ultrashort laser pulses. It is also seen that the entire envelope has a full width of half maximum of about 30 fs that corresponds to the pulse width of the ultrashort laser pulses. From these results it is seen that the present apparatus makes it possible to control the delay time at a precision of 1 fs.

FIG. 4(b) is a graph of the quantity of the probe signal (the amount expressed by equation 2 mentioned above) that is proportional to the differential coefficient of the probe signal, which was measured by the same condition as in FIG. 4(a) where the delay time was modulated with an amplitude $\Delta t_d$ of 0.5 fs and a modulation frequency ω of 400 Hz. It is seen that the waveform of FIG. 4(b) assumes a differential waveform of the waveform of FIG. 4(a). To wit, it is seen that the present apparatus allows the delay time dependent probe signal, namely the delay time dependent probe signal to be measured at a precision of 1 fs.

Thus, with the ability to control the delay time at a precision of 1 fs and then to measure the delay time dependent probe signal at a precision of 1 fs, it is seen that the present apparatus is capable of measuring the delay time dependency of the probe signal at a temporal precision as short as a pulse width of ultrashort laser pulses.

Next, mention is made of a second form of implementation of the present invention.

While the preceding explanation was given in respect of an arrangement in which the delay time between ultrashort laser pulses having an identical wavelength is varied and modulated to directly measure a quantity of the probe signal, mention is made below of an arrangement in which the delay time between ultrashort laser pulses having different wavelengths is varied and modulated to directly measure a quantity of the probe signal.

FIG. 5 is a diagram illustrating the construction of a delay time modulated and femtosecond time-resolved scanning probe microscope apparatus constituting such a second form of implementation of the present invention. In the Figure, the delay time modulated and femtosecond time-resolved scanning probe microscope apparatus of the invention in its second form of implementation is designated by reference character numeral 20 and is characterized by comprising an ultrashort laser pulse generator 21 for producing a series of ultrashort laser pulses 22; an ultrabroadband, variable wavelength, multi-pulse waveform shaping unit 25 which produces from an ultrashort laser pulse 22 produced by the ultrashort laser pulse generator 21, a plurality of ultrashort laser pulses 23 and 24 different in wavelength and interspaced by a delay time and which also is capable of establishing a desired value for the delay time between the ultrashort laser pulses 23 and 24 different in wavelength; a wavelength/delay time/modulation timing control unit 26 which produces a control signal 27 that sets up selected values for the wavelength of the ultrashort laser pulses 23 and 24, a control signal 27 that sets up a selected value for the delay time between the ultrashort laser pulses 23 and 24 and a control signal 27 that modulates the delay time at selected time instants, and delivers such control signals 27 to a two-dimensional space amplitude and a two-dimensional space phase modulator in the ultrabroadband, variable wavelength, pulse waveform shaping unit 25 while furnishing a lock-in detector 8 with a delay time modulation timing signal used as a reference signal 28 for lock-in detection thereby; a scanning probe microscope 7 for scanning a specimen 18 over a surface area thereof with a probe 19 in which the probe 19 is disposed just above the specimen 18 so that a tunnel junction is formed between the probe 19's apex and the specimen 18 irradiated with ultrashort laser pulses 23 and 24 controlled by the wavelength/delay time/modulation timing control unit 26 and transmitted from the ultrabroadband, variable wavelength, pulse waveform shaping unit 25; and the lock-in detection unit 8 which using the modulation timing signal as the reference signal 28 performs lock-in detection of a probe signal 11 from the specimen 18 irradiated with the ultrashort laser pulses 23 and 24 in the scanning probe microscope 7.

While as regards a plurality of ultrashort laser pulses of which a wavelength and between which a delay time are selected, mention is made of two ultrashort laser pulses 23 and 24 in connection with FIG. 5, it should be noted that they are not limited to such two and may be more than two. Further, reference numeral 12 indicates measurement data transmitted from the lock-in detection unit 8 to an image display 13.

FIG. 6 is a diagram showing the makeup of the ultrabroadband, variable wavelength, multi-pulse waveform shaping unit. It corresponds to FIG. 1 contained in PCT International Publication No. WO 01/44863 A1.

Since the ultrabroadband, variable wavelength, multi-pulse waveform shaping unit is described in detail in that patent literature, only a brief review of the same may be sufficient here. For the sake of simplicity of the description, it is assumed that an x-axis extends in a direction parallel to the sheet of the drawing while a y-axis extends in a direction perpendicular thereto. In the Figure, the ultrabroadband, variable wavelength, multi-pulse waveform shaping unit 25 includes an ultrabroadband light pulse generator 31 which converts an ultrashort laser pulses 22 produced by the ultrashort laser pulse generator 21 into an ultrabroadband light pulse; a beam expander 35 which comprises a plurality of cylindrical lenses 32, 33 and a planar mirror 34 and by which the ultrashort laser pulse whose bandwidth is ultrabroadened is expanded in the direction of y-axis; a wavelength dispersing unit 38 which comprises a grating 36 and a cylindrical lens 37 curved in a direction of x-axis and by which the ultrashort laser pulse expanded in the direction of y-axis is collimated and its wavelengths are dispersed in the direction of x-axis; a two-dimensional space amplitude modulator 39 for setting a desired value for the transmissivity of each spot on an x-y plane of the collimated ultrashort laser pulse; a two-dimensional space phase modulator 40 for setting a desired value for the phase of each spot on an x-y plane of the ultrashort laser pulse passed through the two-dimensional space amplitude modulator 39; a beam reducing and waveform shaping unit 43 which comprises a cylindrical lens 41 curved in a direction of x-axis and a grating 42 and by which the ultrashort laser pulse passed through the two-dimensional space phase modulator 40 is reduced in a direction of x-axis and then shaped into a desired pulse waveform.

The ultrabroadband light pulse generator 31 utilizes a higher order nonlinear effect of a nonlinear optical medium and, if made of a tapered quartz fiber extremely thinned in its central part, is capable of widening the bandwidth of an ultrashort laser pulse generated at a high repetition rate by a titanium/sapphire laser (center wavelength 790 nm) from a bandwidth of 500 nm to a bandwidth of 1000 nm.

The two-dimensional space amplitude modulator 39 is formed of an array of pixels made of a liquid crystal on an x-y plane in which the transmissivity of each pixcel can be selectively controlled by changing an applied voltage for each pixcel.

The two-dimensional space phase modulator 40 as is the two-dimensional space amplitude modulator 39 is formed of an array of pixels made of a liquid crystal on an x-y plane in which the reflective index of each pixcel can be selectively controlled by changing an applied voltage for each pixcel.

FIG. 7 diagrammatically illustrates an example of how the transmissivity of the two-dimensional space amplitude modulator 39 may be set. FIG. 7(a) shows an exemplary array of pixels arranged in four rows (y1, y2, y3 and y4) in a direction of y-axis and in twenty columns in a direction of x-axis in which pixels 51 shown in black represent those with their transmissivity set at 0 while pixels 52 shown in white represents those with their transmissivity set at desired values other than 0.

FIG. 7(b) diagrammatically illustrates a spatial distribution of wavelengths and intensities of ultrashort laser pulses transmitted through the two-dimensional space amplitude modulator 39 in which transmissivities of pixels are set as shown in FIG. 7(a). Next, the operation of this unit is briefly described with reference to an example.

As mentioned in connection with FIG. 6, an ultrashort laser pulse incident on the two-dimensional space amplitude modulator 39 is expanded in a direction of y-axis and has its wavelengths dispersed in a direction of x-axis. Thus, if the two-dimensional space amplitude modulator 39 is designed as shown in FIG. 7(a), namely so that in row y1 successive pixels on the left-hand side of the row are transmissive, in row y2 successive pixels somewhat in the middle of the row are transmissive, in row y3 successive pixels in the middle of the row are transmissive and in row y4 successive pixels on the right-hand side of the row are transmissive and if each of these successions of transmissive pixels is so set in each row that the pixel in its center has the highest transmissivity which is gradually reduced pixel by pixel towards the pixels on its left and right hand sides, a single ultrashort laser pulse can be converted through the two-dimensional space amplitude modulator 39 into a plurality of ultrashort laser pulses varying in wavelength and spatially separated from one another as shown in FIG. 7(b).

FIG. 8 diagrammatically illustrates an example of how the phases can be set in the two-dimensional space phase modulator 40. FIG. 8(a) shows an exemplary array of pixels arranged in four rows (y1, y2, y3 and y4) in a direction of y-axis and in twenty columns in a direction of x-axis in which the successions of pixels 61 shown in white correspond, respectively in position, to a plurality of ultrashort laser pulses different in wavelength outgoing from the two-dimensional space amplitude modulator 39 to give them desired phases. FIG. 8(b) shows waveforms of ultrashort laser pulses on time axis (t) which are obtained when partial waves having desired different phases imparted thereto through different pixels 61 are brought together in a direction of x-axis.

An ultrashort laser pulses output from the two-dimensional space amplitude modulator 39 is decomposed through pixels 61 of the two-dimensional space phase modulator 40 into partial waves each of which is then given a desired phase. Since imparting desired different phases to partial waves allows putting the partial waves side by side in a desired order on time axis, it is possible to output ultrashort laser pulses having a desired configuration on time axis. For example, it is possible to form two ultrashort laser pulses having a desired delay time $t_d$ on time axis as shown at row y1 in FIG. 8(b) from an ultrashort laser pulse as shown at row y1 in FIG. 7(b) when desired phases are set for the successive white pixels shown at the left-hand side on row y1 in FIG. 8(a) and resultant partial waves are put together in a direction of x-axis through the cylindrical lens 41 and the grating 42 of FIG. 6.

Likewise, when ultrashort laser pulses as shown respectively at rows y2 and y3 in FIG. 7(b) are decomposed into partial waves through the successive white pixels shown at rows y2 and y3 in FIG. 8(a) and these partial waves having desired phases imparted thereto are put side by side in a desired order on time axis, it is possible to form an ultrashort laser pulse having wavelength λ 2 as shown at row y2 in FIG. 8(b) and an ultrashort laser pulse having wavelength λ 3 as shown at row y3 in the same Figure so that they have a desired delay time $t_d$.

It is thus made possible to obtain a train of ultrashort laser pulses having a desired wavelength or wavelengths and a desired delay time or delay times by expanding an ultrashort laser pulse in a y-direction and having it dispersed in wavelength in a direction of x-axis, decomposing the resultant ultrashort laser pulse through the two-dimensional space phase modulator 39 for each of wavelengths, imparting a desired amplitude to each of the resultant partial waves through the two-dimensional space phase modulator 40, and bringing the resultant ultrashort laser pulses together in a direction of x-axis through the cylindrical lens 41 and the grating 42.

The wavelength/delay time/modulation timing control unit 26 shown in FIG. 5 furnishes the space amplitude modulator 39 and the two-dimensional space phase modulator 40 with a modulation control signal 27 for bringing about a train of ultrashort laser pulses of a desired wavelength or wavelengths and a desired delay time or delay times. It further delivers, alternately with such a modulation control signal, another modulation control signal 27 at a fixed periodicity with which to vary only the delay time incrementally by an amount $\Delta t_d$ expressed by Equation (1), thereby modulating the delay time $t_d$ at such a fixed periodicity. It also furnishes the lock-in detector 8 with timing signals (at a frequency $\omega_M$) as the reference signal 28 to indicate delivery of each of modulation control signals time-delayed by $\Delta t_d$.

Thus, according to the second form of implementation of a delay time modulated, femtosecond time-resolved scanning probe microscope apparatus in which wavelengths are selected for a plurality of ultrashort laser pulses, the delay time between such ultrashort laser pulses is varied and modulated at a fixed periodicity and a lock-in is detected with a delay time modulation frequency, it is possible to directly measure a quantity of the delay time dependent probe signal by irradiations with such a plurality of ultrashort laser pulses which vary in wavelength. According to this apparatus, it is possible to derive knowledge about a photoexcited physical phenomenon in which three or more energy levels are involved, for example, as shown in FIG. 10.

Although the present invention has hereinbefore been set forth with respect to certain illustrative embodiments thereof, it will readily be appreciated to be obvious to those skilled in the art that many alterations thereof, omissions therefrom and additions thereto can be made without departing from the essences of scope of the present invention. Accordingly, it should be understood that the invention is not intended to be limited to the specific embodiments thereof set forth above, but to include all possible embodiments that can be made within the scope with respect to the features specifically set forth in the appended claims and to encompass all the equivalents thereof.

INDUSTRIAL APPLICABILITY

As will be appreciated from the foregoing description, the present invention allows direct measurement of a probe signal component that is dependent on a delay time between ultrashort laser pulses and such measurement unaffected by a fluctuation in the intensity of ultrashort laser pulses, and prevents the probe apex from thermal expansion and shrinkage. It is thus made possible to measure a photoexcited physical phenomenon at a temporal resolution in the order of femtoseconds and at a spatial resolution in the order of angstroms. It is also made possible to directly measure a probe signal component that is dependent on a delay time between ultrashort laser pulses different in wavelength, which therefore allows acquisition of knowledge of a higher order photoexcited physical phenomenon.

The present invention is extremely useful when used for the elucidation of a photoexcited physical phenomenon that occurs in a local area of nanoscale and in a time period in the order of femtoseconds.

What is claimed is:

1. A delay time modulated and femtosecond time-resolved scanning probe microscope apparatus, characterized in that it comprises:
    an ultrashort laser pulse generator;
    a delay time modulating circuit for splitting an ultrashort laser pulse produced by said ultrashort laser pulse generator into two ultrashort laser pulses interspaced by a delay time while establishing a value for the delay time between the two ultrashort laser pulses and modulating the delay time centering about the established value with a fixed modulation frequency;
    a scanning probe microscope for scanning a specimen over a surface area thereof with a probe wherein the probe is disposed just above the specimen so that a tunnel junction is formed between a probe apex and a surface of said specimen when irradiated with said two ultrashort laser pulses modulated by said delay time modulating circuit; and
    a lock-in detection unit for lock-in-detecting a probe signal of the specimen irradiated with said ultrashort laser pulses in said scanning probe microscope using the modulation frequency for the delay time as a reference signal.

2. A delay time modulated and femtosecond time-resolved scanning probe microscope apparatus as set forth in claim 1, characterized in that said ultrashort laser pulse generator is adapted to produce a series of ultrashort laser pulses having a pulse width in the order of femtoseconds at a fixed periodicity.

3. A delay time modulated and femtosecond time-resolved scanning probe microscope apparatus as set forth in claim 1, characterized in that said delay time modulating circuit includes a half mirror and two sets of movable mirrors of which each set comprises mirrors fastened to a piezo stage wherein at least one of said sets of movable mirrors is adapted to be driven to change a center value of the delay time and to modulate the delay time as a center delay time with the fixed frequency.

4. A delay time modulated and femtosecond time-resolved scanning probe microscope apparatus as set forth in claim 1, characterized in that said lock-in detection unit is adapted to perform lock-in detection using the modulation frequency as a reference frequency and thereby to detect a quantity that is proportional to a differential coefficient of said probe signal with respect to said delay time at the center value of said delay time.

5. A delay time modulated and femtosecond time-resolved scanning probe microscope apparatus as set forth in claim 1, characterized in that said scanning probe microscope is a scanning tunneling microscope or an atomic force microscope.

6. A delay time modulated and femtosecond time-resolved scanning probe microscope apparatus, characterized in that it comprises:
    an ultrashort laser pulse generator;
    an ultrabroadband, variable wavelength, multi-pulse waveform shaping unit for producing from an ultrashort laser pulse produced by said ultrashort laser pulse generator, a plurality of ultrashort laser pulses each of that can have different wavelength to others and interspaced by a delay time and establishing a desired value for the delay time between the ultrashort laser pulses different in wavelength;
    a wavelength/delay time/modulation timing control unit for producing a control signal to establish selected values for the wavelength of the ultrashort laser pulses, a control signal to establish a selected value for the delay time between the ultrashort laser pulses and a control signal to modulate the delay time at selected time instants, and delivering such control signals to a two-dimensional space amplitude modulator and a two-dimensional space phase modulator in said ultrabroadband, variable wavelength, multi-pulse waveform shaping unit while furnishing a lock-in detector with delay time modulation timing signals used as a reference signal for lock-in detection thereby;
    a scanning probe microscope for scanning a specimen over a surface area thereof with a probe wherein the probe is disposed just above the specimen so that a tunnel junction is formed between a probe apex and a surface of said specimen when irradiated with said ultrashort laser pulses controlled by said wavelength/delay time/modulation timing control unit and transmitted from said ultrabroadband, variable wavelength, multi-pulse waveform shaping unit; and
    a lock-in detection unit for lock-in-detecting a probe signal of the specimen irradiated with said ultrashort laser pulses in said scanning probe microscope using said modulation timing signals as the reference signal.

7. A delay time modulated and femtosecond time-resolved scanning probe microscope apparatus as set forth in claim 6, characterized in that said wavelength/delay time/modulation timing control unit comprises a computer that is responsive to input values for desired wavelengths of and delay time between said ultrashort laser pulses and an input value for a modulation timing frequency for computing control signals for said two-dimensional space amplitude and phase modulators and transmitting these control signals thereto while furnishing said lock-in detection unit with said modulation timing signals.

8. A delay time modulated and femtosecond time-resolved scanning probe microscope apparatus as set forth in claim 6, characterized in that said lock-in detection unit is configured to perform lock-in detection using said modulation timing signals as a reference frequency and thereby to detect a quantity that is proportional to a differential coefficient of said probe signal with respect to said delay time in said delay time.

9. A delay time modulated and femtosecond time-resolved scanning probe microscope apparatus as set forth in claim 6, characterized in that said scanning probe microscope is a scanning tunneling microscope or an atomic force microscope.

* * * * *